HYPODERMIC NEEDLE CLEANING MACHINES

Original Filed Feb. 12, 1951 2 Sheets-Sheet 1

INVENTOR.
OSCAR WALTER VARGA
BY
ATTORNEY

Aug. 23, 1955 O. W. VARGA Re. 24,054

HYPODERMIC NEEDLE CLEANING MACHINES

Original Filed Feb. 12, 1951 2 Sheets-Sheet 2

INVENTOR.
OSCAR WALTER VARGA
BY

United States Patent Office

Re. 24,054

Reissued Aug. 23, 1955

24,054

HYPODERMIC NEEDLE CLEANING MACHINES

Oscar W. Varga, Englewood, Colo., assignor to Technical Equipment Corporation, Denver, Colo., a corporation of Colorado Original No. 2,636,201, dated April 28, 1953, Serial No. 210,498, February 12, 1951. Application for reissue February 15, 1954, Serial No. 416,732

12 Claims. (Cl. 15—302)

Matter enclosed in heavy brackets [ ] appears in the original patent but forms no part of this reissue specification; matter printed in italics indicates the additions made by reissue.

This invention relates to a hypodermic needle cleaning machine, and is more particularly designed for use in large hospitals and institutions employing an excessive amount of needles. The invention has for its principal object the provision of a substantially automatic mechanism which will subject a continuous supply of hypodermic needles to a successive series of washing, cleansing, and drying steps and then automatically eject the cleansed needles into a receiver without handling or hand operations, and which will have a relatively large needle capacity.

Other objects and advantages reside in the detail construction of the invention, which is designed for simplicity, economy, and efficiency. These will become more apparent from the following description.

In the following detailed description of the invention, reference is had to the accompanying drawing which forms a part hereof. Like numerals refer to like parts in all views of the drawing and throughout the description.

Figure 4:
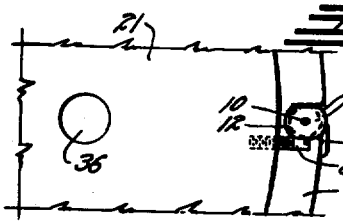
Fig. 4 is a fragmentary, enlarged front view of a portion of a needle wheel employed in the improved machine, illustrating a needle in place therein.
Figure 5:
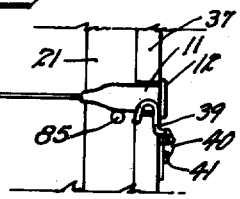
Fig. 5 is a similar fragmentary edge view of the needle wheel.
Figure 6:
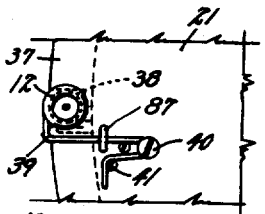
Fig. 6 is a similar fragmentary, rear view of the needle wheel.

In Figs. 4, 5, and 6 a conventional hypodermic needle is illustrated at 10, with its hollow syringe sleeve at 11 and syringe sleeve flange at 12.

The improved needle cleaning machine is mounted on a base plate 13 having a back plate 14, a partition plate 15, and a front plate 16 extending upwardly therefrom. The back plate 14 and the partition plate 15 are relatively narrower than the base plate 13 and support a platform plate 17 thereover. The front plate 16 is relatively wider than the plates 14 and 15 and is provided with a plurality of [bracket members] *brackets* 18 radially positioned about its upper extremity.

A longitudinally movably, rotatable wheel shaft 19 is journalled in the front and back plates 16 and 14 and extends horizontally and longitudinally of the machine through the partition plate 15. The rear extremity of the shaft 19 is secured in a hand wheel 20 by means of which the shaft 19 may be rotated. A circular needle wheel 21 is secured on the forward extremity of the needle shaft by means of a clamp nut 22.

The shaft 19 is constantly urged forwardly, and the needle wheel 21 is caused to rotate through pre-set intervals by means of a rounded plunger 32 which is constantly urged against the rear face of the needle wheel by means of a spring 33 mounted in a spring barrel 34. The spring barrel is secured in the front plate 16 by means of clamping nuts 35. The rounded extremity of the plunger 32 successively engages stop holes 36 of smaller diameter than the plunger, which are formed in an annular series in the needle wheel 21. It can be seen that when rotative pressure is applied to the hand wheel 20, it will cause the rounded extremity of the plunger 32 to slide from one stop hole 36 and snap into the next following stop hole 36 so that the wheel 21 will rotate at intervals, sixteen intervals being illustrated.

The shaft 19 can be forced rearwardly against the action of the spring 33 by means of a handle 30 provided with a handle ball 31. The handle 30 is mounted in a pressure plate 29, from which a bifurcated yoke 26 extends downwardly. The yoke 26 is pivoted on a pivot pin 28 in a notch in the forward extremity of the platform plate 17, and terminates at its lower extremity in two bearing rollers 27 which ride in a circumferential groove in a grooved collar 24. The collar 24 is rotatably and slidably mounted on the shaft 19 between a compression spring 23 and a first set collar 90. The spring 23 is compressed between the grooved collar 24 and a second rear set collar 25. The collars 25 and 90 are secured to the shaft 19 in any desired manner, such as by means of set screws. It can be seen that if the handle 30 is swung forwardly, the yoke 26 will act through the spring 23 to force the needle wheel resiliently rearward toward the front plate 16.

The edge of the needle wheel is provided with a rear circumferential flange 37 in which a plurality of uniformly spaced needle notches 38 are formed corresponding in number to the number of stop holes 36. The needle notches are designed to receive the syringe sleeves 11 of the hypodermic needles 10, as shown in Figs. 4, 5, and 6.

The syringe sleeves 11 of the needles are held in the notches 38 by means of wire latch springs 39 which are formed with U-shaped loops at their one extremities overlying the sleeves 11 of the needles. Each latch spring extends radially inward on the rear face of the needle wheel and about an anchor screw 40, thence terminates around a stop screw 41. The springs are held in place by an overlapping staple 87. It can be seen that the looped extremity of [the] *each* spring 39 can be forced back to allow the syringe [sleeves] *sleeve* 11 of [the needles] *a needle* to be inserted, and *that* the loop in the extremity of the spring will then snap over the sleeve 11 of the needle to retain the latter in the notch 38. The needles are prevented from rotating in the notches 38 of the needle wheel by means of stop screws 85 extending radially from the needle wheel 21 adjacent each of the notches 38 to be engaged by flat sides which are formed on the [bases] *syringe sleeves* of all hypodermic needles.

Figure 1:
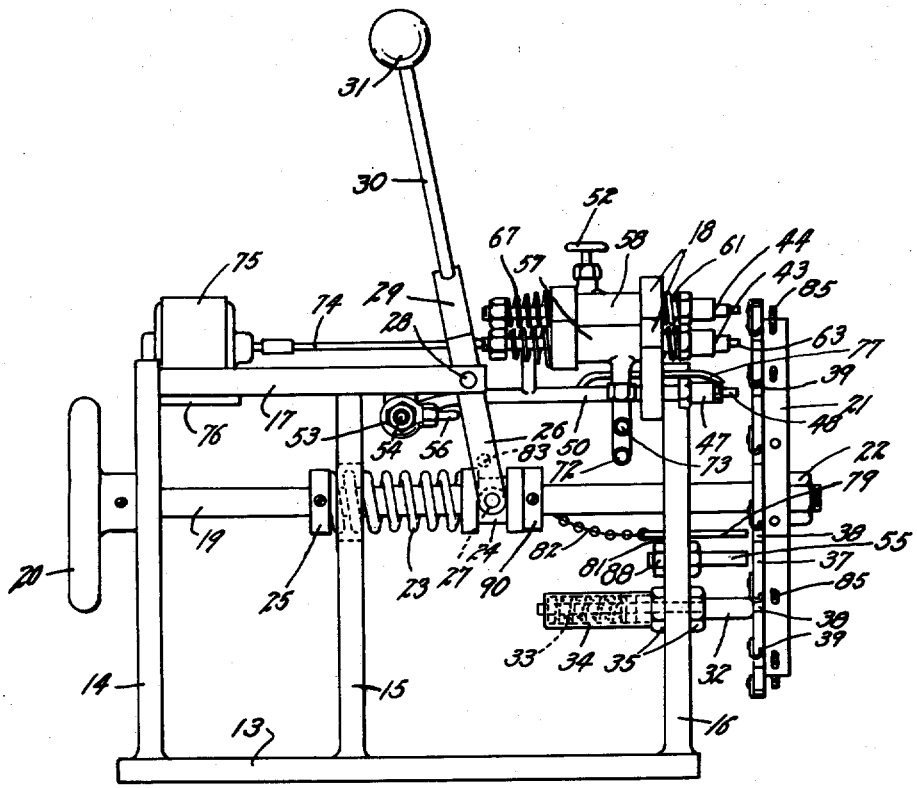
Fig. 1 is a side view of the improved hypodermic needle cleaning machine.
Figure 2:
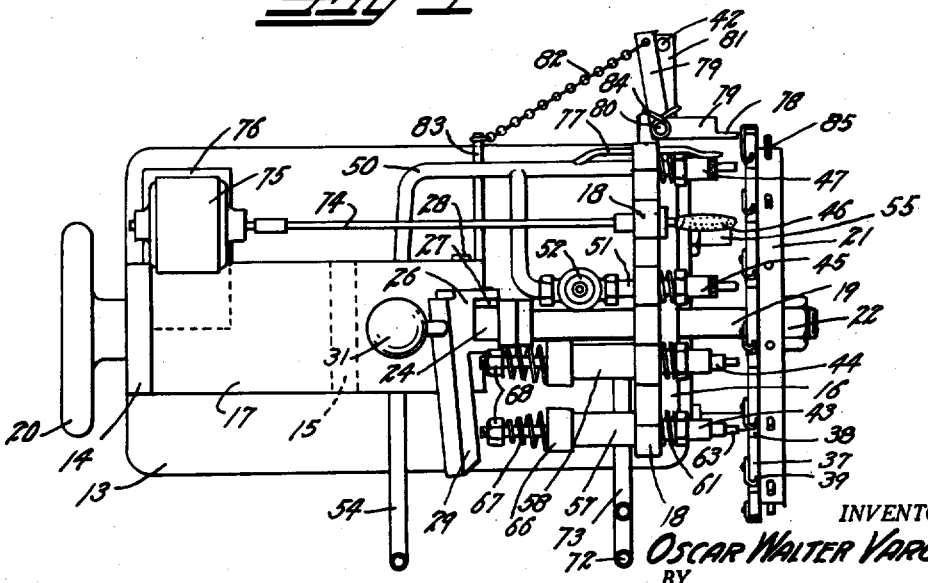
Fig. 2 is a top view thereof.
Figure 3:
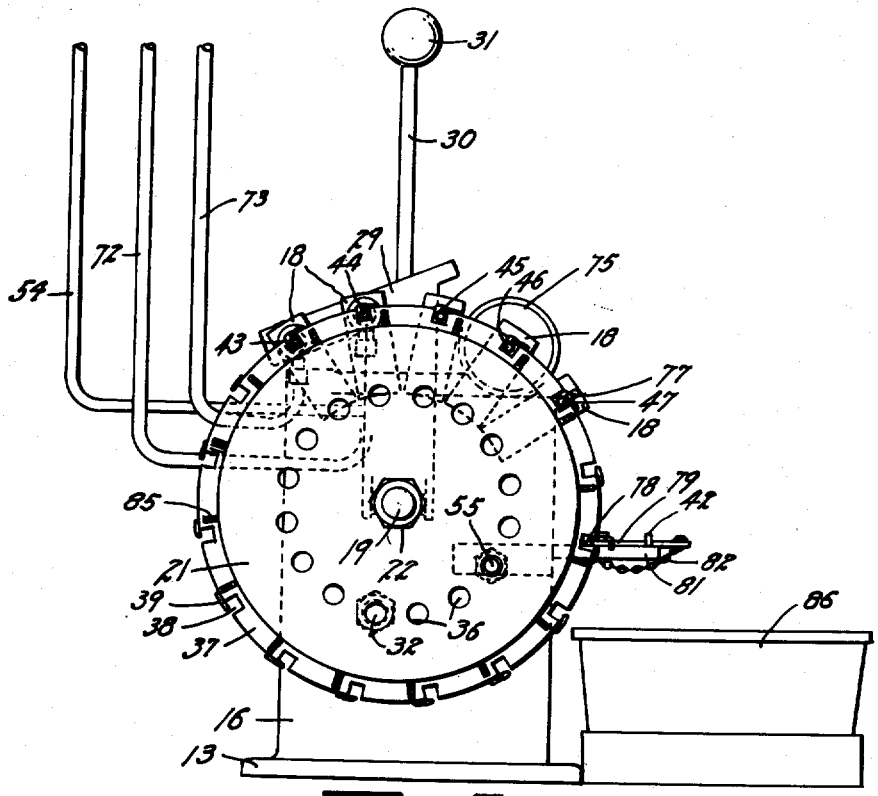
Fig. 3 is a front end view.

The wheel 21 is rotated in a clockwise direction in Fig. 3 so that the needles in the notches 38 are successively brought in front of a detergent nozzle 43, a water nozzle 44, an air nozzle 45, a rotating cleaning swab 46, and a final air nozzle 47. Each of the nozzles and the cleaning swab 46 is supported in one of the brackets 18 about the periphery of the needle wheel 21 and in alignment with the interval positions of the notches 36.

Figure 8:
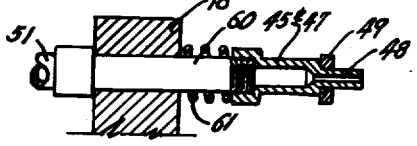
Fig. 8 is a similarly enlarged section through an air or water nozzle used in the improved machine.

The air nozzles 45 and 47 are similar in construction and are illustrated more in detail in Fig. 8. Each nozzle is formed with a tip portion 48 surrounded by a resilient washer 49. The nozzles are mounted on the forward extremities of straight nipples 60 which extend through [the] *their* respective brackets 18. The nipple of the nozzle 47 is connected to an air pipe 50, and the nozzle 45 is connected to a second air pipe 51. The air pipe 51 takes its air from the pipe 50, and the flow through the pipe 51 [is adjustable] *may be regulated* by means of a control valve 52. A cushion spring 61 is positioned between each of the nozzles 45 and 47 and their respective brackets 18 so that the nozzles may move resiliently inward toward [its bracket] *their respective brackets.*

When the handle 30 is forced forwardly, the needles in the notches 38 will be forced rearwardly so that their [collars] *sleeves* 11 will pass over the [tips] *tip portions* 48 of the nozzles 45 and 47 to allow the syringe sleeve flanges 12 to seal against the resilient washers 49 under the compression of the *cushion* springs 61.

The air pipe 50 extends from a push-type valve 53 secured beneath the platform plate 17 and provided with a valve opening plunger 56. The valve 53 is supplied with air from any suitable source through an air supply main 54. The push valve 53 is so positioned that its opening plunger 56 will be in the path of the yoke 26 so that as the yoke swings rearwardly to retract the wheel 21, the plunger 56 will be contacted to open the valve 53 and supply air to the two air nozzles 45 and 47.

Figure 7:
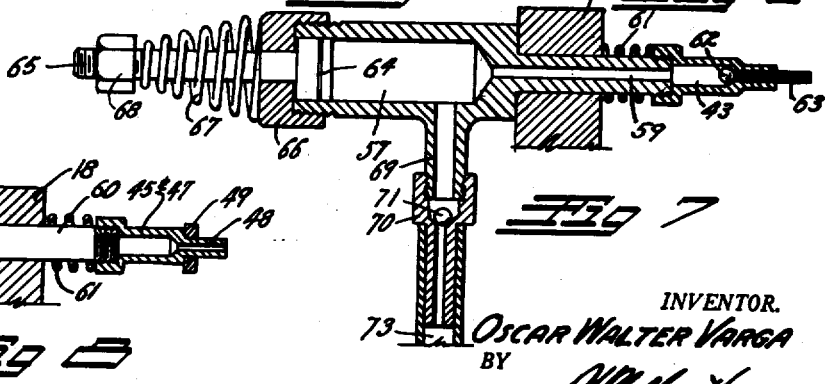
Fig. 7 is an enlarged, longitudinal section through a pumping mechanism employed on the improved machine.

The detergent nozzle 43 is supplied with detergent fluid from a detergent pump 57, and the water nozzle 44 is supplied with water from a water pump 58. In Fig. 7 a longitudinal section of the detergent pump 57 is illustrated. It is to be understood that a cross-section of the water pump 58 would be similar to that illustrated in this figure.

The pumps 57 and 58 are formed with reduced forward extremities 59 which slidably extend through their respective brackets 18. The nozzles 43 and 44 are threaded onto the forward ends of the reduced extremities 59 and one of the cushion springs 61, similar to those used on the air nozzles, is positioned between each nozzle and its respective [arm] *bracket* so that the nozzle may be forced resiliently inward.

Each nozzle is normally closed by means of a [ball valve] *valve ball* 62 which can be forced from its seat by means of a hollow push tube 63, one of which extends forwardly from each of the nozzles 43 and 44. The inner end of each push tube is notched so that its hollow interior will not be sealed by the ball 62.

Each of the pumps 57 and 58 is provided with a pump piston 64 mounted on a piston rod 65 which extends rearwardly through a cylinder head cap 66 on each pump. The pistons 64 are constantly urged rearwardly in the pumps by means of helical springs 67 acting against spring nuts 68 on the piston rods 65.

Fluid is admitted to each of the pumps through a bottom nipple 69 closed by a hose nipple 70. A check valve ball 71 is positioned in each hose nipple 70 to prevent fluid from flowing away from the pumps. A water supply hose 72 conducts water to the water pump 58, and a detergent supply hose 73 conducts detergent fluid to the detergent pump 57 from any suitable elevated source.

It can be readily seen that rearward movement of the wheel 21 will cause the [needle collars] *syringe sleeves* 11 to pass onto the tips of the nozzles 43 and 44. In so doing, the push tubes 63 will be forced inwardly to open the ball valves 62. Further forward movement of the handle 30 causes the [needle] *syringe* sleeves *of the needles* to seat over the nozzles 43 and 44 and *acts* to force the latter [inward] *inwardly* against the springs 61 until the pressure plate 29 contacts the rear extremities of the piston rods 65 to force both pistons 64 forwardly in their respective pumps. This forces predetermined amounts of water and detergent fluid through the respective nozzles 44 and 43 and through push tubes 63 into the needles 10.

When the handle 30 is released, the wheel 21 moves away from the nozzles 43 and 44, and the pressure plate 29 moves away from the piston rods 65 to allow the springs 67 to return the pistons 64. Water and detergent fluid then flows from the respective supply hoses 72 and 73 to lift the valve balls 71 and refill the pumps.

After the needles have been subjected to the detergent solution from the nozzle 43 and to the washing solution from the nozzle 44, they pass in front of the first air nozzle 45, which directs a blast of compressed air through the needle to remove any moisture therefrom. The needle then moves in front of the cleaning swab 46, which is mounted on the forward extremity of a swab shaft 74 extending from the shaft of an electric motor 75 mounted on a motor platform 76 supported from the platform plate 17.

The motor 75 is operating continuously during the operation of the needle cleaning machine, so that when the needle wheel 21 moves rearwardly, the [collar] *sleeve* portion of each needle will pass over the rotating swab so that the latter will loosen and clean out any foreign material in the [collar] *sleeve*. The [collar] *sleeve* is prevented from rotating with the swab by the stop screw 85 which is engaging a flat side of the [base] *sleeve* of the needle.

From the swab the needle passes to the second air nozzle 47, which directs a blast of air into the needle to remove any adhering foreign material loosened by the swab. An auxiliary air jet 77 is positioned adjacent to, and exteriorly of, the air nozzle 47 to remove any adhering material from the exterior of the needle.

The needle then passes in front of an ejector pin 78 formed on one extremity of an L-shaped ejector arm 79. The ejector arm is mounted by means of a pivot screw 80 upon an ejector bracket 81 supported from the front plate 16. The other extremity of the ejector arm is connected by means of a flexible member, such as a chain 82, with a chain arm 83 extending from one side of the yoke 26. The ejector pin 78 is constantly urged toward the axis of the shaft 19 by means of a hinge spring 84, the inward movement of the ejector pin being limited by a stop screw 42 in the bracket 81.

It can be seen that when the handle 30 is moved forwardly to pull the needle wheel 21 rearwardly, the lower extremity of the yoke 26 wil swing rearwardly, causing the chain arm 83 to tighten the chain 82 so as to swing the ejector pin 78 to the right in Fig. 3 so as to pull the needle sleeve 11 from its engagement with the retaining spring 39. The cleansed needle will fall from the wheel 21 into any suitable receiving receptacle, such as indicated at 86.

A safety stud 55 is mounted on the front plate 16 by means of suitable mounting nuts 88. The stud is positioned in alignment with the stop holes 36 and at the proper stopping position for the needles. The diameter of the stud is just sufficient to allow one of the holes 36 to pass thereover when in the proper position. The stud contacts and prevents the needle wheel from moving rearwardly unless the needles are in exact position over the nozzles and other equipment.

The stiffness of the compression spring 23 exceeds that of the combined springs 61 and 33 so that the latter springs will be compressed before the spring 23 compresses. The spring 23, however, prevents the machine and the needles from being damaged by an inexperienced operator attempting to force the handle forwardly with excessive pressure. The springs 61 accommodate variations in lengths of needle sleeves and prevent damage to misplaced needles.

It will be noted that the needles are not touched by human hands from the time they are inserted in their receiving notches 38, and that they are successively submitted to a detergent cleaning, a washing to remove the detergent, an air blast to remove the water, a swabbing to remove loosened dry material, and an air blast to remove the final material loosened by the swab, so that they are delivered to the receptacle 86 in a perfectly cleansed condition.

While the machine has been illustrated with a hand wheel 20 for rotating the needle wheel 21, it is conceivable that the shaft 19 may be rotated from a motor or other device through a clutch operated by the rearward movement of the shaft 19 so that the only manual operation necessary will be forcing the handle 30 forwardly after each needle has been inserted.

While a specific form of the improvement has been illustrated and described herein, it is to be understood that the same may be varied, within the scope of the appended claims, without departing from the spirit of the invention.

Having thus described the invention, what is claimed and desired secured by Letters Patent is:

1. A device for cleaning hypodermic needles and the like, comprising: a rotatable and longitudinally movable shaft; a needle wheel mounted on one extremity of said shaft; shaft-rotating means mounted on the other extremity of said shaft; a spring urging said shaft [forwardly] *axially in one direction*; a pivoted yoke member mounted adjacent to and engaging said shaft for forcing the latter *axially in the opposite direction* [rearwardly] against the action of said spring; means about the periphery of said wheel for supporting hypodermic needles in spaced relation thereabout; a stationary frame member positioned *axially* [rearwardly] of said wheel to be approached by the latter *when moved axially in said opposite direction*; nozzle supporting means mounted on said frame member so that the nozzles supported thereby will be in alignment with the needles in said wheel so as to engage the latter when said wheel moves [rearwardly] *axially in said opposite direction*; and means for supplying cleaning solutions to said nozzles.

2. A needle cleaning device as described in claim 1 having pumping means mounted on said frame member, said pumping means being arranged to be actuated by *an axial* [the rearward] movement of said wheel to supply cleaning fluid through said nozzles to said needles.

3. A hypodermic cleaning device as described in claim 2 and having discharge valves mounted in said nozzles; and valve-opening means adapted to be contacted by said needles for opening said valves as said wheel moves *axially in said opposite direction* [rearwardly].

4. A needle cleaning machine as described in claim 1 having conduits supplying cleaning fluid to said nozzles; a push-operated valve controlling the flow through said conduits; and means for opening said valve in consequence of *an axial* [the rearward] movement of said wheel.

5. A hypodermic needle cleaning machine as described in claim 2 having a rotating swab device supported by said frame member in alignment with a position of said needles in said wheel so that as said wheel moves *axially in said opposite direction* [rearwardly], said needles will engage said swab for cleaning foreign material therefrom.

*6. A hypodermic needle cleaning machine comprising: a rotatable needle wheel; a plurality of hypodermic needle supporting devices mounted on said wheel and positioned in spaced relation in a concentric path about the axis of said wheel for receiving and supporting hypodermic needles rigidly parallel to the axis of said wheel and across the plane of said wheel and in concentric spaced-relation thereon; a non-rotatable frame member positioned in spaced relation to said wheel; a plurality of nozzles supported by said frame member in alignment with the path of the needles supported by said needle supporting devices; means for rotating said wheel in intervals to align said needles successively with said nozzles; means for supplying fluids to said nozzles; and means for bringing the aligned needles and nozzles into fluid conductive relationship so that fluid from said nozzles will enter said needles at one face of said wheel and discharge therefrom at the opposite face of said wheel.*

*7. A hypodermic needle cleaning machine comprising: a rotatable needle wheel; a plurality of hypodermic needle supporting devices mounted on the periphery of said wheel and acting to support needles about said wheel with the fluid intake extremities of said needles on the first side of the plane of said wheel and with the fluid discharge extremities of said needles on the second side of the plane of said wheel in concentric spaced-relation thereon; a non-rotatable frame member positioned in spaced relation to the first side of said wheel; a first fluid nozzle supported by said frame member; a second fluid nozzle supported by said frame member, said nozzles being supported in alignment with the path of the needles supported by said needle supporting devices; means for rotating said wheel in intervals to align a given needle first with the first fluid nozzle thence with the second fluid nozzle; means for supplying fluids to said nozzles; and means for bringing said given needle into sealed fluid conductive relationship with each nozzle when the needle is aligned therewith so that fluid will be forced completely through said needle so as to discharge on the second side of said wheel.*

*8. A hypodermic needle cleaning machine comprising: a rotatable needle wheel; a plurality of hypodermic needle supporting devices mounted on said wheel and positioned in spaced relation in a concentric path about the axis of said wheel for receiving and supporting hypodermic needles rigidly parallel to the axis of, and across the plane of, said wheel in concentric spaced-relation thereon; a non-rotatable frame member positioned in spaced relation to said wheel; a plurality of nozzles supported by said frame member in alignment with the path of the needles supported by said needle supporting devices; means for rotating said wheel in intervals to align said needles successively with said nozzles; means for supplying fluids to said nozzles; and means for moving said wheel toward and away from said frame member to bring the aligned needles into and out of sealed fluid conductive relationship with said nozzles so that fluid will be forced into said needles at one face of said wheel and discharged therefrom at the other face of said wheel.*

*9. A hypodermic needle cleaning machine comprising: a plurality of fixedly positioned spaced-apart fluid ejecting nozzles; a movable needle carrier; means for supporting a hypodermic needle upon said carrier rigidly perpendicular to the plane of said carrier and across the plane thereof so as to position the intake extremity of said needle on the first side of said plane and the discharge extremity thereof on the second side of said plane; means for moving said carrier at intervals transversely of said nozzles so as to align said needle with each of said nozzles in succession; and means for moving said carrier toward said nozzles as said needle aligns with each nozzle to bring said needle into fluid conductive relationship with each nozzle so that fluid may be forced from each nozzle from the first side of said carrier through said needle so as to discharge from the second side of said carrier.*

*10. In a machine for successively cleaning a plurality of hypodermic needles comprising: a plurality of relatively spaced fluid nozzles; means for supplying a cleaning fluid to one of said nozzles; means for supplying a rinsing fluid to a second nozzle; means for supplying air to a third nozzle; fluid-sealing seating means carried by said nozzles; a carrier provided with similarly spaced means for holding said plurality of needles; means for optionally positioning said carrier with the ends of said needles in and out of fluid conductive association with said nozzles; means for imparting movement to said carrier transversely of said nozzles in intervals corresponding to the spacing of said needles and nozzles so that each needle will align with the first nozzle, the second nozzle and the third nozzle in succession; and means for controlling the supplies of fluids to said nozzles in consequence of the positioning of the ends of said needles in and out of fluid conductive association with said nozzles, so that each needle will be successively subjected to cleaning fluid, rinsing fluid and air as it passes transversely of said needles.*

*11. A device for cleaning hypodermic needles and the like, comprising: a rotatable and longitudinally movable shaft; a needle wheel mounted on one extremity of*

*said shaft; shaft-rotating means mounted on said shaft; a spring urging said shaft axially in one direction; a yoke member mounted adjacent to and engaging said shaft for forcing the latter axially in the opposite direction against the action of said spring; means about the periphery of said wheel for supporting hypodermic needles in spaced relation thereabout; a stationary frame member positioned axially of said wheel to be approached by the latter when moved axially in said opposite direction; nozzle supporting means mounted on said frame member so that the nozzles supported thereby will be in alignment with the needles in said wheel so as to engage the latter when said wheel moves axially in said opposite direction; and means for supplying cleaning solutions to said nozzles.*

*12. A machine for cleansing hypodermic needles of the type having intake and discharge extremities comprising: means for holding a plurality of needles in parallel uniform spaced relation with their intake extremities facing rearwardly; a plurality of similarly spaced fluid nozzles positioned rearwardly of said needle holding means; means acting to move said plurality of needles rearwardly into sealed fluid conductive relation with said*

*nozzles so that fluid will be forced completely through said needles to flow from the discharge extremities thereof; and means for transversely moving said plurality of needles successive spaces equal to the spacing of said cleansing devices.*

References Cited in the file of this patent or the original patent

UNITED STATES PATENTS

| | | |
|---|---|---|
| 524,053 | Anderson | Aug. 7, 1894 |
| 768,492 | Tunelius | Aug. 23, 1904 |
| 843,056 | Young | Feb. 5, 1907 |
| 981,962 | Wehmiller | Jan. 17, 1911 |
| 1,470,712 | Demmler | Oct. 16, 1923 |
| 1,520,110 | Blakeslee | Dec. 23, 1924 |
| 1,644,384 | Kendall | Oct. 4, 1927 |
| 1,800,533 | Hummel | Apr. 14, 1931 |
| 2,014,750 | Stegemann | Sept. 17, 1935 |
| 2,107,474 | Everett | Feb. 8, 1938 |

FOREIGN PATENTS

| | | |
|---|---|---|
| 66,732 | Sweden | Aug. 5, 1926 |
| 292,027 | Great Britain | June 14, 1928 |